US008557815B2

(12) United States Patent
Harbeson

(10) Patent No.: US 8,557,815 B2
(45) Date of Patent: Oct. 15, 2013

(54) SUBSTITUTED TRIAZOLOPHTHALAZINE DERIVATIVES

(75) Inventor: Scott L. Harbeson, Cambridge, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 123 days.

(21) Appl. No.: 12/856,360

(22) Filed: Aug. 13, 2010

(65) Prior Publication Data

US 2011/0172235 A1 Jul. 14, 2011

Related U.S. Application Data

(60) Provisional application No. 61/233,964, filed on Aug. 14, 2009.

(51) Int. Cl.
*A61K 31/5025* (2006.01)
*C07D 487/04* (2006.01)

(52) U.S. Cl.
USPC .......................................... 514/248; 544/234

(58) Field of Classification Search
None
See application file for complete search history.

(56) References Cited

U.S. PATENT DOCUMENTS

| 6,200,975 | B1 | 3/2001 | Carling et al. |
| 6,221,335 | B1 | 4/2001 | Foster |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2007/0082929 | A1 | 4/2007 | Gant et al. |
| 2007/0197533 | A1* | 8/2007 | Zhou et al. ............... 514/241 |
| 2007/0197695 | A1 | 8/2007 | Potyen et al. |
| 2008/0103122 | A1 | 5/2008 | Veltri |

FOREIGN PATENT DOCUMENTS

| WO | WO 95/26325 A2 | 10/1995 |
| WO | WO99/25353 A1 | 5/1999 |
| WO | WO 02/42305 A1 | 5/2002 |
| WO | WO 2007/118651 A1 | 10/2007 |

OTHER PUBLICATIONS

Baillie, T. A., "The Use of Stable Isotopes in Pharmacological Research," *Pharmacological Reviews*, 33(2): 81-132 (1981).
Browne, T. R., "Stable Isotope Techniques in Early Drug Develop-ment: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," *Curr. Opin. Drug Discov. Devel.*, 9(1): 101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Kushner, D.J. et al., "Pharmacological Uses and Perspectives of Heavy Water and Deuterated Compounds," *Can. J. Physiol. Pharmacol.*, 77:79-88 (1999).
Park, B.K., et al., "Metabolism of Fluorine-Containing Drugs," *Annu. Rev. Pharmacol. Toxicol.*, 41:443-470 (2001).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Toren G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Wolen, R. L., "The Application of Stable Isotopes to Studies of Drug Bioavailability and Bioequivalence," *J. Clin. Pharmacol.*, 26: 419-424 (1986).
Notification of Transmittal of the International Search Report and the Written Opinion of the International Searching Authority, or the Declaration; International Application No. PCT/US2010/045508; Date of Mailing: Sep. 30, 2010.

* cited by examiner

*Primary Examiner* — Emily Bernhardt
(74) *Attorney, Agent, or Firm* — Edwards Wildman Palmer LLP; Jeffrey D. Hsi; Mark D. Russett

(57) ABSTRACT

This invention relates to novel substituted triazolophthalazines and pharmaceutically acceptable salts thereof. This invention also provides compositions comprising a compound of this invention and the use of such compositions in methods of treating diseases and conditions that are beneficially treated by administering selective α5 receptor partial or full inverse agonists.

5 Claims, No Drawings

SUBSTITUTED TRIAZOLOPHTHALAZINE DERIVATIVES

RELATED APPLICATION

This application claims the benefit of U.S. Provisional Application No. 61/233,964 filed on Aug. 14, 2009, the entire teachings of which are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

$GABA_A$ receptors are ligand-gated chloride channels that mediate the inhibitory effects of γ-aminobutyric acid (GABA) in the CNS. $GABA_A$ receptors are heteromeric proteins of five subunits primarily found as receptors containing α, β, and γ subunits in a 2:2:1 stoichiometry. $GABA_A$ receptors containing the α1, α2, α3, or α5 subunits contain a binding site for benzodiazepines, which is the basis for the pharmacologic activity of benzodiazepines. An α5 receptor partial or full inverse agonist that is relatively free of activity at al and/or α2 and/or α3 receptor binding sites can be used as a therapeutic agent that enhances cognition but has reduced or eliminated sedative and/or proconvulsant effects.

An example of such a selective α5 receptor partial or full inverse agonist is the compound α5IA, also known as 3-(5-methylisoxazol-3-yl)-6-[(1-methyl-1,2,3-triazol-4-yl)methyloxy]-1,2,4-triazolo[3,4-a]phthalazine and as 5-methyl-3-(6-((1-methyl-1H-1,2,3-triazol-4-yl)methoxy)-[1,2,4]triazolo[3,4-a]phthalazin-3-yl)isoxazole. Despite the beneficial activities of known α5 receptor partial or full inverse agonists, there is a continuing need for new compounds that have beneficial effects as cognition enhancers without sedative and proconvulsant effects.

SUMMARY OF THE INVENTION

This invention relates to novel substituted triazolophthalazines and pharmaceutically acceptable salts thereof. The compounds of this invention are selective partial or full inverse agonists for $GABA_A$ receptors containing the α5 subunit and are therefore useful as therapeutics related to cognition enhancement. This invention also provides compositions comprising a compound of this invention and the use of such compositions in methods of treating diseases and conditions that are beneficially treated by administering an α5 receptor partial or full inverse agonist.

DETAILED DESCRIPTION OF THE INVENTION

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

The term "hydrocarbyl" refers to a monovalent hydrocarbon group which is a $C_1$-$C_6$ alkyl, a $C_2$-$C_6$ alkenyl, or a $C_2$-$C_6$ alkynyl, as these terms are defined herein below.

The term "halogen" refers to fluorine, chlorine, bromine or iodine.

The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

The term "alkenyl" refers to a monovalent unsaturated hydrocarbon group where the unsaturation is represented by a double bond. $C_2$-$C_6$ alkenyl is an alkenyl having from 2 to 6 carbon atoms. An alkenyl may be linear or branched. Examples of alkenyl groups include $CH_2$=CH—, $CH_2$=C($CH_3$)—, $CH_2$=CH—$CH_2$—, $CH_3$—CH=CH—$CH_2$—, $CH_3$—CH=C($CH_3$)— and $CH_3$—CH=CH—CH($CH_3$)—$CH_2$—. Where double bond stereoisomerism is possible, the stereochemistry of an alkenyl may be (E), (Z), or a mixture thereof.

The term "alkynyl" refers to a monovalent unsaturated hydrocarbon group where the unsaturation is represented by a triple bond. $C_2$-$C_6$ alkynyl is an alkynyl having from 2 to 6 carbon atoms. An alkynyl may be linear or branched. Examples of alkynyl groups include CH≡C—, —C≡C($CH_3$), $CH_3$—C≡C—$CH_2$—, $CH_3$—C≡C—$CH_2$—$CH_2$ and $CH_3$—C≡C—CH($CH_3$)—$CH_2$—.

The term "carbocyclyl" refers to a monocyclic or bicyclic monovalent saturated or non-aromatic unsaturated hydrocarbon ring system. The term "$C_3$-$C_{10}$ carbocyclyl" refers to a carbocyclyl wherein the number of ring carbon atoms is from 3 to 10. Examples of $C_3$-$C_{10}$ carbocyclyl include $C_3$-$C_6$ carbocyclyl. Bicyclic ring systems include fused, bridged, and spirocyclic ring systems. More particular examples of carbocyclyl groups include, cyclopropyl, cyclobutyl, cyclopentyl, cyclopentenyl, cyclohexyl, cyclohexenyl, cycloheptyl, cis- and trans-decalinyl, norbornyl, norbornenyl, and spiro [4.5]decanyl.

The term "heterocyclyl" refers to a monocyclic or bicyclic monovalent saturated or non-aromatic unsaturated ring system wherein from 1 to 4 ring atoms are heteroatoms independently selected from the group consisting of O, N and S. The term "3 to 10-membered heterocyclyl" refers to a heterocyclyl wherein the number of ring atoms is from 3 to 10. Examples of 3 to 10-membered heterocyclyl include 3 to 6-membered heterocyclyl. Bicyclic ring systems include fused, bridged, and spirocyclic ring systems. More particular examples of heterocyclyl groups include azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, and thiomorpholinyl.

The term "heteroaryl" refers to a monovalent aromatic monocyclic ring system wherein at least one ring atom is a heteroatom independently selected from the group consisting of O, N and S. The term 5-membered heteroaryl refers to a heteroaryl wherein the number of ring atoms is 5. Examples of 5-membered heteroaryl groups include pyrrolyl, pyrazolyl, oxazolyl, isoxazolyl, thiazolyl, isothiazolyl, oxadiazolyl, thiadiazolyl, furazanyl, imidazolinyl, and triazolyl.

It will be recognized that some variation of natural isotopic abundance occurs in a synthesized compound depending upon the origin of chemical materials used in the synthesis. Thus, a preparation of α5IA will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound.

In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free of another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", and "t-" each refer to tertiary. "US" refers to the United States of America.

The term "substituted with deuterium" means that one or more hydrogen atoms in the indicated moiety are substituted with a deuterium atom.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

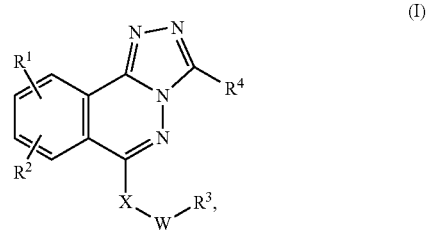

or a pharmaceutically acceptable salt thereof, wherein:

$R^1$ and $R^2$ are each independently selected from hydrogen, halogen, —CN, —$CF_3$, —$OCF_3$ and $C_1$-$C_4$ alkyl, wherein each $C_1$-$C_4$ alkyl is optionally substituted with one or more deuterium and is optionally substituted with one or two Z;

each Z is independently selected from halogen, cyano, amino and —$CF_3$;

$R^3$ is a 5-membered heteroaryl containing 1, 2, 3 or 4 heteroatoms independently selected from oxygen, nitrogen and sulfur, wherein $R^3$ is optionally substituted with one or more groups selected from halogen, —CN, —$CF_3$, —$R^5$, —$OR^5$, —$OC(O)R^5$, —$NR^6R^7$ and $NR^6C(O)R^7$;

$R^4$ is a 5-membered heteroaryl containing 1, 2 or 3 heteroatoms independently selected from oxygen, nitrogen and sulfur, provided that when one of the heteroatoms is oxygen or sulfur, $R^4$ contains at least one nitrogen, wherein $R^4$ is optionally substituted with one or more groups selected from deuterium, halogen, —CN, —$R^8$, —$NR^9R^{10}$ or $NR^9C(O)R^{10}$;

each $R^5$ is independently H, deuterium, hydrocarbyl or $C_3$-$C_{10}$ carbocyclyl, wherein each $R^5$ hydrocarbyl and $C_3$-$C_{10}$ carbocyclyl is independently optionally substituted with one or more deuterium, optionally substituted with one or more hydroxyl, and optionally substituted with one to four halogens;

$R^6$ and $R^7$ are each independently selected from hydrogen, hydrocarbyl, $C_3$-$C_{10}$ carbocyclyl, and $CF_3$, wherein each $R^6$ and $R^7$ hydrocarbyl and $C_3$-$C_{10}$ carbocyclyl is optionally independently substituted with one or more deuterium; or the $R^6$ and $R^7$ of —$NR^6R^7$ together with the nitrogen atom to which they are attached form a 3 to 10-membered heterocyclyl;

$R^8$ is selected from $CF_3$, hydrocarbyl, and $C_3$-$C_{10}$ carbocyclyl, wherein each $R^8$ independently is optionally substituted with one or more deuterium, optionally substituted with one or more hydroxyl, and optionally substituted with one to four halogens;

$R^9$ and $R^{10}$ are each independently selected from hydrogen, hydrocarbyl, $C_3$-$C_{10}$ carbocyclyl, and $CF_3$; wherein each $R^9$ and $R^{10}$ hydrocarbyl and $C_3$-$C_{10}$ carbocyclyl is optionally independently substituted with one or more deuterium; or $R^9$ and $R^{10}$, together with the nitrogen atom to which they are attached, form a 3 to 10-membered heterocyclyl;

$R^{11}$ is selected from hydrogen, deuterium, hydrocarbyl or $C_3$-$C_{10}$ carbocyclyl, wherein $R^{11}$ hydrocarbyl and $C_3$-$C_{10}$ carbocyclyl are optionally substituted with one or more deuterium, optionally substituted with one or more hydroxyl, and optionally substituted with one to four halogens;

W is —$(CY^1Y^2)_n$— wherein n is 1, 2 or 3 and each Y is independently selected from hydrogen or deuterium; and X is selected from O, S and $NR^{11}$;

with the proviso that if each Y is hydrogen, then at least one R comprises deuterium.

In one embodiment, $R^1$ and $R^2$ are independently hydrogen or fluorine. In one aspect of this embodiment, $R^1$ and $R^2$ are each hydrogen.

In one embodiment, $R^3$ is a 5-membered heteroaryl containing 1, 2 or 3 nitrogens and is optionally substituted with one or more $R^5$. In one aspect of this embodiment, $R^1$ and $R^2$ are independently hydrogen or fluorine. In another aspect of this embodiment, $R^1$ and $R^2$ are each hydrogen.

In another embodiment, $R^3$ is selected from imidazolyl, pyrazolyl, 1,2,3-triazolyl, and 1,2,4-triazolyl and is optionally substituted with one or more $R^5$. In one aspect of this embodiment, $R^1$ and $R^2$ are independently hydrogen or fluorine. In another aspect of this embodiment, $R^1$ and $R^2$ are each hydrogen.

In one embodiment, $R^4$ is selected from pyrrolyl, pyrazolyl, oxazolyl, isoxazolyl, thiazolyl, isothiazolyl, oxadiazolyl, and thiadiazolyl and is optionally substituted with one or more $R^8$. In one aspect of this embodiment, $R^1$ and $R^2$ are independently hydrogen or fluorine. In another aspect of this embodiment, $R^1$ and $R^2$ are each hydrogen. In yet another aspect, $R^3$ is a 5-membered heteroaryl containing 1, 2 or 3 nitrogens and is optionally substituted with one or more $R^5$. In a further aspect of this embodiment, $R^3$ is a 5-membered heteroaryl containing 1, 2 or 3 nitrogens and is optionally substituted with one or more $R^5$; and $R^1$ and $R^2$ are independently hydrogen or fluorine. In another aspect of this embodiment, $R^3$ is a 5-membered heteroaryl containing 1, 2 or 3 nitrogens and is optionally substituted with one or more $R^5$; and $R^1$ and $R^2$ are each hydrogen. In still another aspect of this embodiment, $R^3$ is selected from imidazolyl, pyrazolyl, 1,2,3-triazolyl, and 1,2,4-triazolyl and is optionally substituted with one or more $R^5$; and $R^1$ and $R^2$ are independently hydrogen or fluorine. In another aspect of this embodiment, $R^3$ is selected from imidazolyl, pyrazolyl, 1,2,3-triazolyl, and 1,2,4-triazolyl and is optionally substituted with one or more $R^5$; and $R^1$ and $R^2$ are each hydrogen.

In another embodiment, $R^4$ is selected from isoxazolyl or oxadiazolyl and is optionally substituted with one or more groups independently selected from —$CH_3$, —$CD_3$, —$CH_2OH$, —$CD_2OH$, —$CH_2F$ and —$CD_2F$. In one aspect of this embodiment, $R^1$ and $R^2$ are independently hydrogen or fluorine. In another aspect of this embodiment, $R^1$ and $R^2$ are each hydrogen. In yet another aspect, $R^3$ is a 5-membered heteroaryl containing 1, 2 or 3 nitrogens and is optionally substituted with one or more $R^5$. In a further aspect of this embodiment, $R^3$ is a 5-membered heteroaryl containing 1, 2 or 3 nitrogens and is optionally substituted with one or more $R^5$; and $R^1$ and $R^2$ are independently hydrogen or fluorine. In another aspect of this embodiment, $R^3$ is a 5-membered heteroaryl containing 1, 2 or 3 nitrogens and is optionally substituted with one or more $R^5$; and $R^1$ and $R^2$ are each hydrogen. In still another aspect of this embodiment, $R^3$ is selected from imidazolyl, pyrazolyl, 1,2,3-triazolyl, and 1,2,4-triazolyl and is optionally substituted with one or more $R^5$; and $R^1$ and $R^2$ are independently hydrogen or fluorine. In another aspect of this embodiment, $R^3$ is selected from imidazolyl, pyrazolyl, 1,2,3-triazolyl, and 1,2,4-triazolyl and is optionally substituted with one or more $R^5$; and $R^1$ and $R^2$ are each hydrogen.

In one embodiment, $R^5$ is hydrogen or $C_1$-$C_6$ alkyl optionally substituted with one or more deuterium. In one aspect, $R^5$ is hydrogen or $C_1$-$C_6$ alkyl optionally substituted with one or more deuterium in any one of the embodiments or aspects described above.

In another embodiment, $R^5$ is hydrogen or $C_1$-$C_3$ alkyl optionally substituted with one or more deuterium. In one aspect, $R^5$ is hydrogen or $C_1$-$C_3$ alkyl optionally substituted with one or more deuterium in any one of the embodiments or aspects described above.

In one embodiment, $R^8$ is selected from $C_1$-$C_6$ alkyl and $R^8$ is optionally substituted with one or more deuterium and optionally substituted with one hydroxyl. In one aspect, $R^8$ is selected from $C_1$-$C_6$ alkyl and $R^8$ is optionally substituted with one or more deuterium and optionally substituted with one hydroxyl in any one of the embodiments or aspects described above.

In one embodiment, $Y^1$ and $Y^2$ are the same. In one aspect, $Y^1$ and $Y^2$ are the same in any one of the embodiments or aspects described above.

In another embodiment, each of $Y^1$ and $Y^2$ is hydrogen. In one aspect, each of $Y^1$ and $Y^2$ is hydrogen in any one of the embodiments or aspects described above.

In another embodiment, each of $Y^1$ and $Y^2$ is deuterium. In one aspect, each of $Y^1$ and $Y^2$ is deuterium in any one of the embodiments or aspects described above.

In one embodiment, W is —$CH_2$— or —$CD_2$-. In one aspect, W is —$CH_2$— or —$CD_2$- in any one of the embodiments or aspects described above.

In another embodiment, W is —$CD_2$-. In one aspect, W is —$CD_2$- in any one of the embodiments or aspects described above.

In one embodiment, X is selected from O and $NR^5$. In one aspect of this embodiment, X is selected from O and $NR^{11}$ in any one of the embodiments or aspects described above.

In another embodiment, X is oxygen. In one aspect of this embodiment, X is selected from 0 in any one of the embodiments or aspects described above.

In one embodiment, $R^1$ and $R^2$ are independently hydrogen or fluorine; $R^3$ is a 5-membered heteroaryl containing 1, 2 or 3 nitrogens and is optionally substituted with one or more $R^5$; $R^4$ is selected from pyrrolyl, pyrazolyl, oxazolyl, isoxazolyl, thiazolyl, isothiazolyl, oxadiazolyl, and thiadiazolyl and is optionally substituted with one or more $R^8$; $R^5$ is hydrogen or $C_1$-$C_6$ alkyl optionally substituted with one or more deuterium; $R^8$ is selected from $C_1$-$C_6$ alkyl and $R^8$ is optionally substituted with one or more deuterium and optionally substituted with one hydroxyl; W is —CH$_2$— or —CD$_2$-; and X is selected from O and NR$^5$.

In one embodiment, R$^1$=R$^2$=hydrogen;

R$^3$ is selected from imidazolyl, pyrazolyl, 1,2,3-triazolyl, and 1,2,4-triazolyl and is optionally substituted with one or more R$^5$;

R$^4$ is selected from isoxazolyl or oxadiazolyl and is optionally substituted with one or more groups independently selected from —CH$_3$, —CD$_3$, —CH$_2$OH, —CD$_2$OH, —CH$_2$F and —CD$_2$F;

R$^5$ is hydrogen or C$_1$-C$_3$ alkyl optionally substituted with one or more deuterium; and X is oxygen.

In one embodiment, the invention is directed to a compound of Formula Ia,

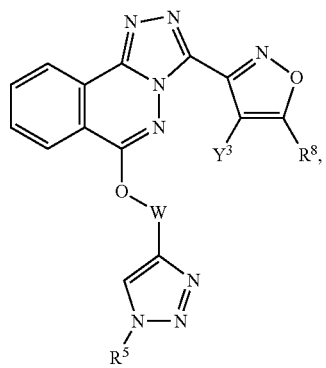

(Ia)

or a pharmaceutically acceptable salt thereof, wherein:

R$^5$ is selected from methyl and ethyl, each optionally substituted with one or more deuterium;

R$^8$ is methyl, optionally substituted with one or more deuterium;

W is —CY$^1$Y$^2$—, wherein Y$^1$ and Y$^2$ are the same and are selected from hydrogen and deuterium; and Y$^3$ is hydrogen or deuterium;

provided that when R$^5$ is —CH$_3$ or —CH$_2$CH$_3$, R$^8$ is —CH$_3$, and Y$^3$ is hydrogen, then W is —CD$_2$-.

In one embodiment of formula Ia, R$^5$ is CD$_3$. In another embodiment, R$^5$ is CH$_3$. In another embodiment, R$^5$ is CH$_2$CH$_3$. In another embodiment, R$^5$ is CD$_2$CD$_3$.

In one embodiment of formula Ia, R$^8$ is CH$_3$. In another embodiment, R$^8$ is CD$_3$.

Specific examples of compounds of Formula Ia (where Y$^3$ is hydrogen) include those shown in Table Ia below. Specific examples of compounds of Formula Ia (where Y$^3$ is deuterium) include those shown in Table Ib below.

TABLE Ia

| Compound | W | R$^5$ | R$^8$ |
| --- | --- | --- | --- |
| 101 | CH$_2$ | CD$_3$ | CH$_3$ |
| 102 | CD$_2$ | CH$_3$ | CD$_3$ |
| 103 | CH$_2$ | CH$_3$ | CD$_3$ |
| 104 | CH$_2$ | CD$_3$ | CD$_3$ |
| 105 | CD$_2$ | CD$_3$ | CD$_3$ |
| 106 | CH$_2$ | CD$_2$CD$_3$ | CH$_3$ |
| 107 | CD$_2$ | CH$_2$CH$_3$ | CD$_3$ |
| 108 | CH$_2$ | CH$_2$CH$_3$ | CD$_3$ |
| 109 | CH$_2$ | CD$_2$CD$_3$ | CD$_3$ |
| 110 | CD$_2$ | CD$_2$CD$_3$ | CD$_3$ | or a pharmaceutically acceptable salt of any of the foregoing.

TABLE Ib

| Compound | W | R$^5$ | R$^8$ |
| --- | --- | --- | --- |
| 111 | CH$_2$ | CD$_3$ | CH$_3$ |
| 112 | CD$_2$ | CH$_3$ | CD$_3$ |
| 113 | CH$_2$ | CH$_3$ | CD$_3$ |
| 114 | CH$_2$ | CD$_3$ | CD$_3$ |
| 115 | CD$_2$ | CD$_3$ | CD$_3$ |
| 116 | CH$_2$ | CD$_2$CD$_3$ | CH$_3$ |
| 117 | CD$_2$ | CH$_2$CH$_3$ | CD$_3$ |
| 118 | CH$_2$ | CH$_2$CH$_3$ | CD$_3$ |
| 119 | CH$_2$ | CD$_2$CD$_3$ | CD$_3$ |
| 120 | CD$_2$ | CD$_2$CD$_3$ | CD$_3$ | or a pharmaceutically acceptable salt of any of the foregoing.

In another embodiment, the invention provides a compound of the following formula

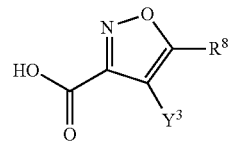

wherein Y$^3$ and R$^8$ are as defined in Formula Ia, provided that when Y$^3$ is hydrogen, then R$^8$ comprises deuterium.

In another embodiment, the invention provides a compound of the following formula

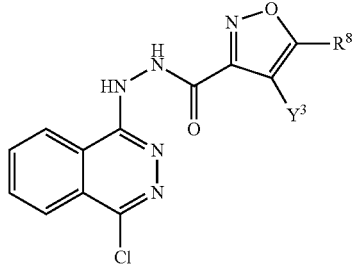

wherein Y$^3$ and R$^8$ are as defined in Formula Ia, provided that when Y$^3$ is hydrogen, then R$^8$ comprises deuterium.

In another embodiment, the invention provides a compound of the following formula

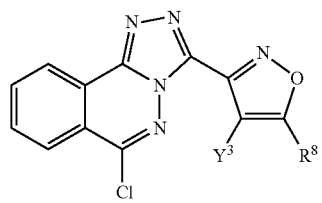

wherein Y$^3$ and R$^8$ are as defined in Formula Ia, provided that when Y$^3$ is hydrogen, then R$^8$ comprises deuterium.

In another embodiment, the invention provides a compound of the following formula

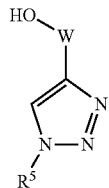

wherein W and $R^5$ are each as defined in Formula I or Ia, provided that when W is —$CH_2$—, $R^5$ comprises deuterium.

In another embodiment, the invention provides a compound of the following formula

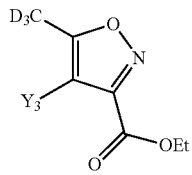

wherein $Y^3$ is as defined in Formula Ia.

In another set of embodiments, any atom not designated as deuterium in any of the embodiments set forth above is present at its natural isotopic abundance.

The synthesis of compounds of Formula I can be readily achieved by synthetic chemists of ordinary skill by reference to the Exemplary Synthesis disclosed herein.

Exemplary Synthesis

Compounds of Formula I can be prepared according to the methods disclosed by Steinfeld, F et al., J. Med. Chem. 2004, 47, pp. 2176-2179; Carling, W R et al., Int. PCT Publication WO98/50385; and Carling, W R et al., Int. PCT Publication WO99/06407. As non-limiting illustrations, the preparation of compounds of Formula Ia is shown in Schemes 1-3.

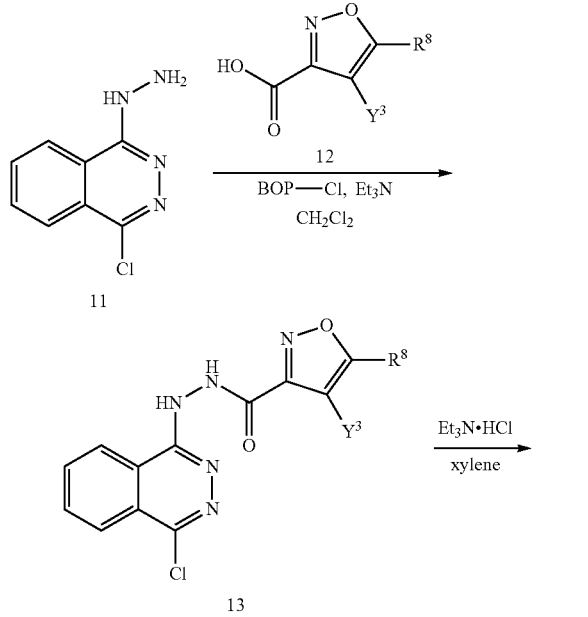

Scheme 1. Preparation of Compounds of Formula Ia.

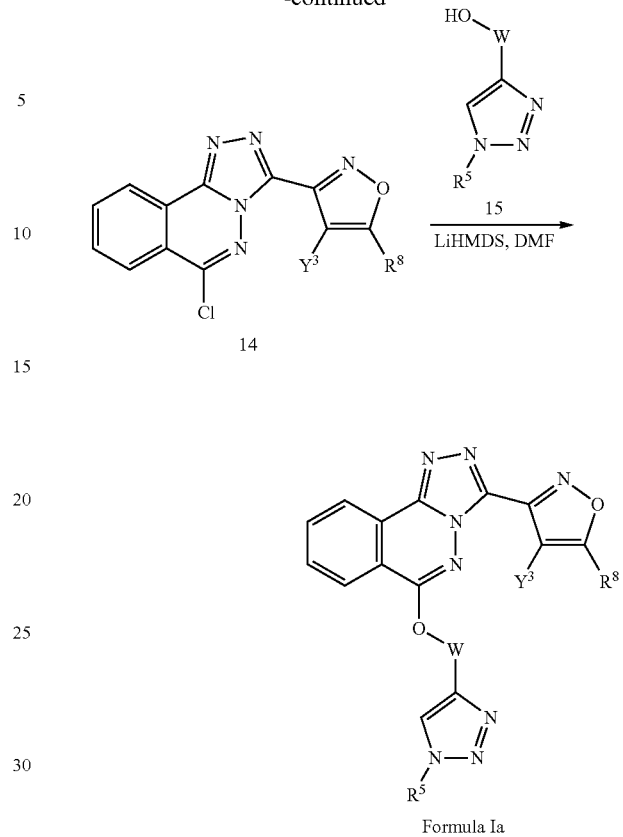

Compounds of Formula Ia may be prepared as depicted in Scheme 1. Amine 11 (prepared from commercially-available 1,4-dichlorophthalazine as described in Steinfeld, F. et al., J. Med. Chem., 2004, 47, pp. 2176-2179) may be coupled with an appropriately-substituted carboxylic acid 12 using bis(2-oxo-3-oxazolidinyl)phosphinic chloride (BOP-Cl) to provide intermediate 13. Cyclization via treatment with catalytic triethylamine hydrochloride yields intermediate 14. Addition of the anion of alcohol 15, formed via treatment of 15 with lithium hexamethyldisilazide (LiHMDS), provides compounds of Formula Ia.

Intermediate 15, for use in Scheme 1, may be prepared as depicted in Scheme 2 below.

Scheme 2 depicts the preparation of intermediate 15, which is of use in Scheme 1. Alkylation of triazole 17 (prepared as described in Sternfeld, F et al., J. Med. Chem. 2004, 47, pp. 2176-2179) with appropriate alkyl iodide 18 affords triazole 19. Reduction of the ester with either LiAlH₄ or LiAlD₄ affords intermediate 15.

A deuterated version of intermediate 12, used in Scheme 1, can be prepared according to the method shown in Scheme 3 below.

Scheme 3. Preparation of a Deuterated Version of Intermediate 12.

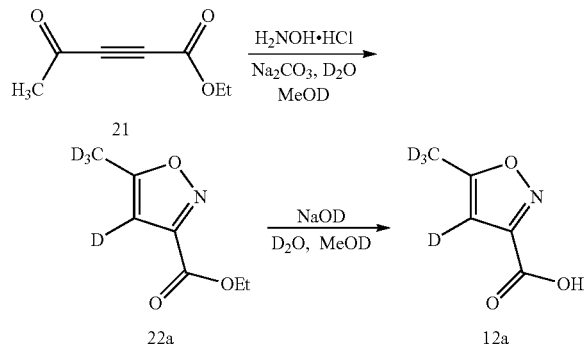

Scheme 3 depicts the preparation of intermediate 12a. Ketone 21 (prepared as described by Persson, T. et al., Org. Lett. 2006, 8(15), pp. 3219-3222) may be converted to isoxazole 22 in a manner analogous to the procedure described by Mitani, M; et al., Eur. J. Org. Chem. 2008, 8, pp. 1383-1391. Performing this reaction in deuterated solvents should provide the desired isoxazole 22. Alternatively, commercially-available hydroxylamine-d3 deuteriochloride may be useful in this step to provide high levels of deuterium incorporation. Base hydrolysis of the ester in deuterated solvent provides the desired carboxylic acid 12.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound that is a selective α5 receptor partial or full inverse agonist.

Preferably, the second therapeutic agent is an agent useful in the treatment or prevention of a disease or condition selected from anxiety, convulsions, skeletal muscle spasm, spasticity, athetosis, epilepsy, stiff-person syndrome, other disorders of the central nervous system, and pain.

Examples of pain include acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, and cancer pain. More particular examples include femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain. For example, the pain may be pain selected from the group consisting of fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

In one embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.01 to about 5000 mg per treatment. In more specific embodiments the range is from about 0.1 to 2500 mg, or from 0.2 to 1000 mg, or most specifically from about 1 to 500 mg. Treatment typically is administered one to three times daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a disease that is beneficially treated by a partial or full inverse agonist of the α5 subunit of the $GABA_A$ receptor in a subject comprising the step of administering to said subject an effective amount of a compound of this invention or a pharmaceutically acceptable salt of said compound or a composition of this invention. Such diseases are well known in the art and are disclosed in, but not limited to the following patents and published applications: WO 1998004559, WO 2000044752, WO 2006061428 and U.S. Pat. No. 6,630,471. Such diseases include, but are not limited to, anxiety, convulsions, skeletal muscle spasm, spasticity, athetosis, epilepsy, stiff-person syndrome, other disorders of the central nervous system, and pain (e.g., neuropathic pain, inflammatory pain, and migraine-associated pain). In a particular embodiment, the disease is selected from anxiety and convulsions.

The term subject can include a patient in need of treatment.

In one embodiment, the disease is pain selected from the group consisting of: acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head pain, neck pain, severe or intractable pain, nociceptive pain, breakthrough pain, postsurgical pain, and cancer pain.

In another embodiment, the pain is selected from the group consisting of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, including abdominal, pancreatic, and IBS pain; chronic and acute headache pain; migraine; tension headache, including cluster headaches; chronic and acute neuropathic pain, including post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including abdominal pain, pyelonephritis, appendicitis, cholecystitis, intestinal obstruction, and hernias; chest pain, including cardiac pain; pelvic pain; renal colic pain; acute obstetric pain, including labor pain; cesarean section pain; acute inflammatory, burn and trauma pain; acute intermittent pain, including endometriosis; acute herpes zoster pain; sickle cell anemia; acute pancreatitis; breakthrough pain; orofacial pain including sinusitis pain and dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC); prostatitis; complex regional pain syndrome (CRPS), type I and type II; and angina-induced pain.

In yet another embodiment, the pain is selected from the group consisting of: fibromyalgia, acute herpes zoster pain, HIV-associated neuropathy, neuropathic low back pain, chemotherapy induced neuropathic pain, radiotherapy-induced neuropathic pain, peripheral nerve injury, spinal cord injury pain, and multiple sclerosis (MS) pain.

Methods delineated herein also include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to said subject one or more second therapeutic agents. The choice of second therapeutic agent may be made from any second therapeutic agent known to be useful for co-administration with a compound that with a compound that is a selective α5 receptor partial or full inverse agonist. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I, or a pharmaceutically acceptable salt of said compound, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I for use in the treatment or prevention in a subject of a disease, disorder or symptom thereof delineated herein.

EXAMPLES

Example 1

Synthesis of 4-d-5-Methyl-$d_3$-3-(6-((1-methyl-$d_3$-1H-1,2,3-triazol-4-yl)methoxy-$d_2$-[1,2,4]triazolo[3,4-a]phthalazin-3-yl)isoxazole (Compound 115)

The synthesis of Compound 115, as described in detail below, is representative of the general synthetic route followed for the preparation of Compounds of Formula I.

Scheme 4. Preparation of Compound 115.

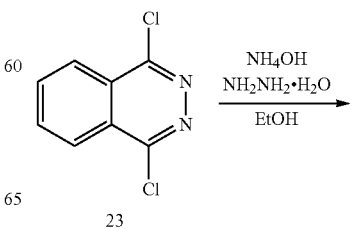

23

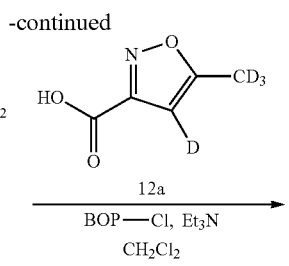

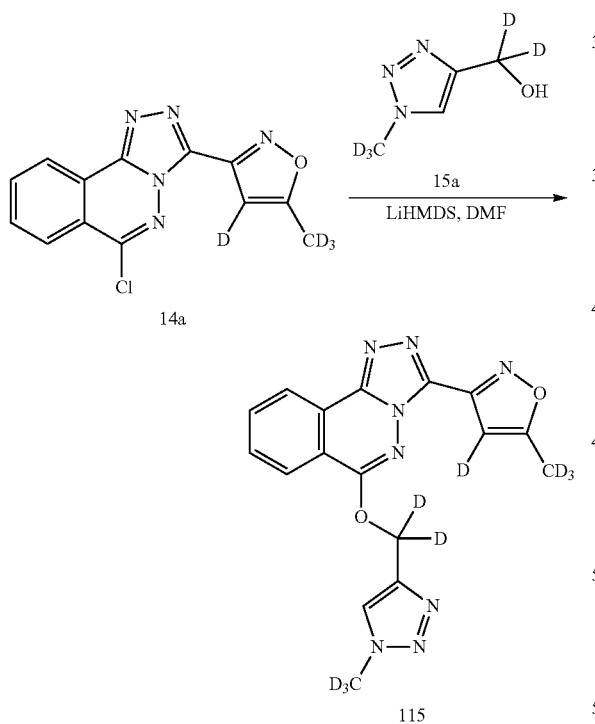

Step 1. 1-Chloro-4-hydrazinylphthalazine (11)

A mixture of 1,4-dichlorophthalazine 23 (10.2 g, 51.2 mmol) and ammonium hydroxide (4.5 mL) in ethanol (110 mL) was heated to 60° C. Hydrazine hydrate (9 mL, 179 mmol) was added dropwise. After about one-half of the hydrazine hydrate was added, a thick precipitate formed. The mixture was stirred well and the temperature was kept below 74° C. by controlled addition of reagent. After the addition was complete the reaction was heated at reflux for 10 min, then allowed to cool. The reaction was filtered and the solids were washed with water (20 mL) and ethanol (20 mL), then dried at 40° C. in a vacuum oven overnight. The crude material was recrystallized from acetonitrile to afford 8.38 g (84%) of 11 as a yellow solid.

Step 2. N'-(4-Chlorophthalazin-1-yl)-4-d-5-methyl-d₃-isoxazole-3-carbohydrazide (13a)

A solution of 11 (240 mg, 1.22 mmol) in $CH_2Cl_2$ (2 mL) was cooled to 0° C. in an ice bath. Compound 12a (160 mg, 1.22 mmol, prepared as in Example 13 below), bis(2-oxo-3-oxazolidinyl)phosphinic chloride (BOP-Cl, 310 mg, 1.22 mmol) and triethylamine (340 µL, 2.44 mmol) were sequentially added. The mixture was stirred cold for 2 hr, then was allowed to warm to room temperature and was stirred overnight. The reaction mixture was concentrated and the residue was diluted with water. The mixture was filtered and the solids were washed with heptane and dried in a vacuum oven to provide 320 mg of crude 13a as a yellow solid that was used without further purification.

Step 3. 3-(6-Chloro-[1,2,4]triazolo[3,4-a]phthalazin-3-yl)-4-d-5-methyl-d₃-isoxazole (14a)

A mixture of crude 13a (1.22 mmol) and triethylamine hydrochloride (0.12 g) in xylenes was heated at reflux for 2-3 hr. The reaction was cooled and concentrated to remove most of the xylenes. The residue was dissolved in $CH_2Cl_2$ (50 mL) and washed with water (2×10 mL). The organic layer was dried ($Na_2SO_4$) and concentrated. The crude material was recrystallized from $CH_2Cl_2$/hexanes to provide 110 mg (37% for 2 steps) of 14a as a light yellow solid.

Step 4. 4-d-5-Methyl-d₃-3-(6-((1-methyl-d₃-1H-1,2,3-triazol-4-yl)methoxy-d₂)-[1,2,4]triazolo[3,4-a]phthalazin-3-yl)isoxazole (115)

Compound 15a (10-13 mg, prepared as described in Example 20) in anhydrous DMF (1 mL) was cooled in an ice/ethanol bath. LiHMDS (1M in THF, 90 µL, 90 mmol) was added and the solution was stirred for 30 min. 14a (20 mg, 0.07 mmol) was added in one portion, and the mixture was allowed to warm to room temperature and was stirred for 1 hr. The reaction was quenched with water. The solids were isolated by filtration, washed with water, and dried to provide approximately 20 mg of crude 115. ¹H-NMR (300 MHz, $CDCl_3$): δ 7.80 (t, J=6.2, 1H), 7.94 (t, J=6.1, 1H), 8.24 (d, J=8.1, 1H), 8.65 (d, J=7.4, 1H), 8.74 (s, 1H). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.91 min; >90% purity. MS (M+H): 372.3.

Example 2

Synthesis of 5-Methyl-d₃-3-(6-((1-methyl-d₃-1H-1,2,3-triazol-4-yl)methoxy-d₂)[1,2,4]triazolo[3,4-a]phthalazin-3-yl)isoxazole (Compound 105)

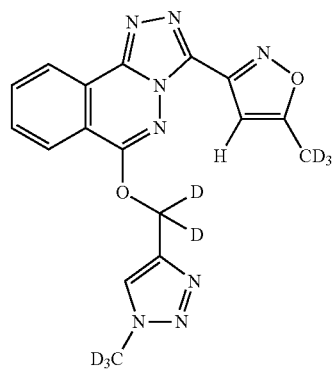

105

Compound 105 was prepared in an analogous fashion to 115 using intermediate 12b (prepared as described in Example 14). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.97 min; >89% purity. MS (M+H): 371.4.

Example 3

Synthesis of 4-d-5-Methyl-d₃-3-(6-((1-methyl-d₃-1H-1,2,3-triazol-4-yl)methoxy)-[1,2,4]triazolo[3,4-a]phthalazin-3-yl)isoxazole (Compound 114)

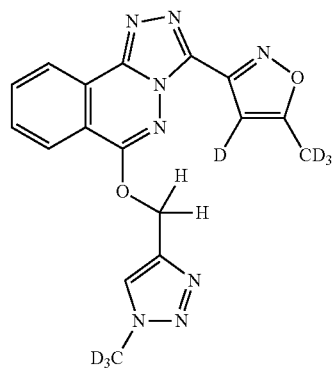

114

Compound 114 was prepared in an analogous fashion to 115 using 15d (prepared as described in Example 21). HPLC (method: RP 20 mm C18—gradient method 2—95% ACN+0.1% formic acid in 3.3 min with 1.7 min hold at 95% ACN+

0.1% formic acid; wavelength: 254 nm): retention time: 2.92 min; >88% purity. MS (M+H): 370.2.

Example 4

Synthesis of 4-d-5-Methyl-d₃-3-(6-((1-methyl-1H-1,2,3-triazol-4-yl)methoxy)-[1,2,4]triazolo[3,4-a]phthalazin-3-yl)isoxazole (Compound 113)

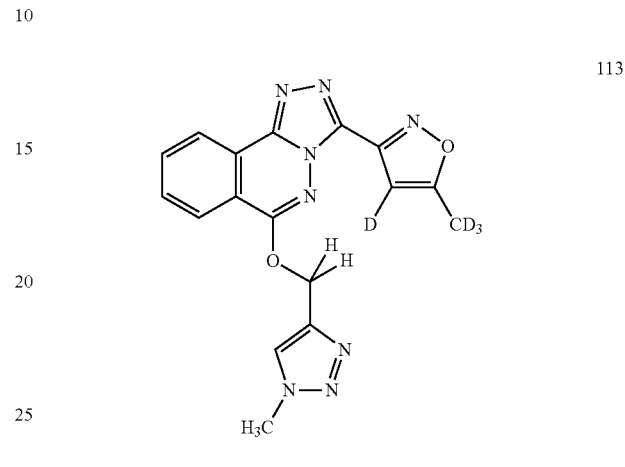

113

Compound 113 was prepared in an analogous fashion to 115 using 15e (prepared as described in Example 22). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.80 min; >87% purity. MS (M+H): 367.2.

Example 5

Synthesis of 4-d-5-Methyl-d₃-3-(6-((1-methyl-1H-1,2,3-triazol-4-yl)methoxy)-[1,2,4]triazolo[3,4-a]phthalazin-3-yl)isoxazole (Compound 101)

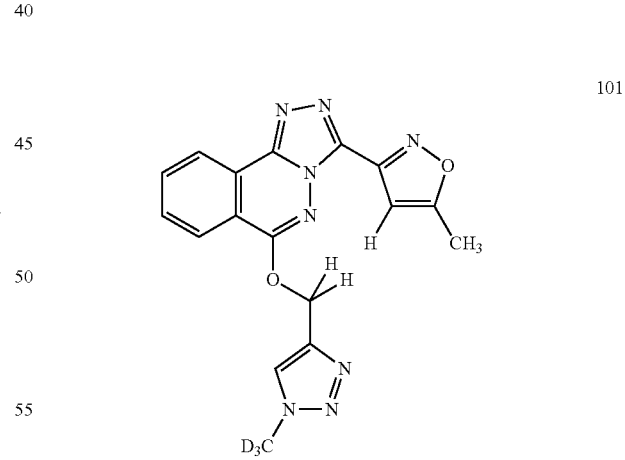

101

Compound 101 was prepared in an analogous fashion to 115 using known compound 6-chloro-3-(5-methyl-3-isoxazolyl)-1,2,4-triazolo[3,4-a]phthalazine (14b, prepared as described in Example 16) and 15d (prepared as described in Example 21). ¹H-NMR (300 MHz, CDCl₃): δ 2.61 (s, 3H), 5.77 (s, 2H), 6.90 (s, 1H), 7.79 (t, J=6.2, 1H), 7.94 (t, J=6.8, 1H), 8.24 (d, J=7.6, 1H), 8.65 (d, J=7.4, 1H), 8.73 (s, 1H). HPLC (method: RP 20 mm C18—gradient method 2—95% ACN+0.1% formic acid in 3.3 min with 1.7 min hold at 95%

ACN+0.1% formic acid; wavelength: 254 nm): retention time: 2.80 min; >92% purity. MS (M+H): 366.0.

Example 6

Synthesis of 4-d-5-Methyl-d$_3$-3-(6-((1-methyl-d$_3$-1H-1,2,3-triazol-4-yl)methoxy)-[1,2,4]triazolo[3,4-a]phthalazin-3-yl)isoxazole (Compound 104)

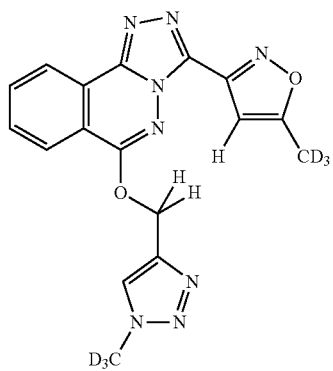

104

Compound 104 was prepared in an analogous fashion to 115 using intermediate 12b (prepared as described in Example 14) and 15d (prepared as described in Example 21). $^1$H-NMR (300 MHz, CDCl$_3$): δ 5.77 (s, 2H), 6.91 (s, 1H), 7.80 (t, J=7.4, 1H), 7.94 (t, J=7.5, 1H), 8.25 (d, J=7.6, 1H), 8.66 (d, J=7.9, 1H), 8.73 (s, 1H). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.81 min; >91% purity. MS (M+H): 369.0.

Example 7

Synthesis of 4-d-5-Methyl-d$_3$-3-(6-((1-methyl-1H-1,2,3-triazol-4-yl)methoxy)-[1,2,4]triazolo[3,4-a]phthalazin-3-yl)isoxazole (Compound 103)

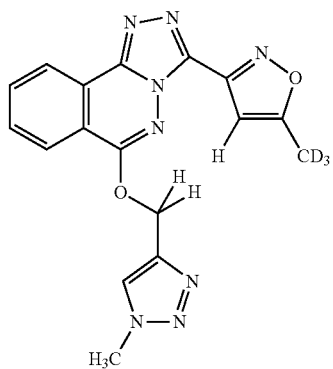

103

Compound 103 was prepared in an analogous fashion to 115 using intermediate 12b (prepared as described in Example 14) and 15e (prepared as described in Example 22). $^1$H-NMR (300 MHz, CDCl$_3$): δ 4.09 (s, 3H), 5.77 (s, 2H), 6.91 (s, 1H), 7.80 (t, J=7.4, 1H), 7.94 (t, J=7.3, 1H), 8.25 (d, J=8.0, 1H), 8.65 (d, J=7.9, 1H), 8.73 (s, 1H). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.83 min; >94% purity. MS (M+H): 366.0.

Example 8

Synthesis of 3-(6-((1-Ethyl-d$_5$-1H-1,2,3-triazol-4-yl)methoxy-d$_2$)-[1,2,4]triazolo[3,4-a]phthalazin-3-yl)-4-d-5-methyl-d$_3$-isoxazole (Compound 120)

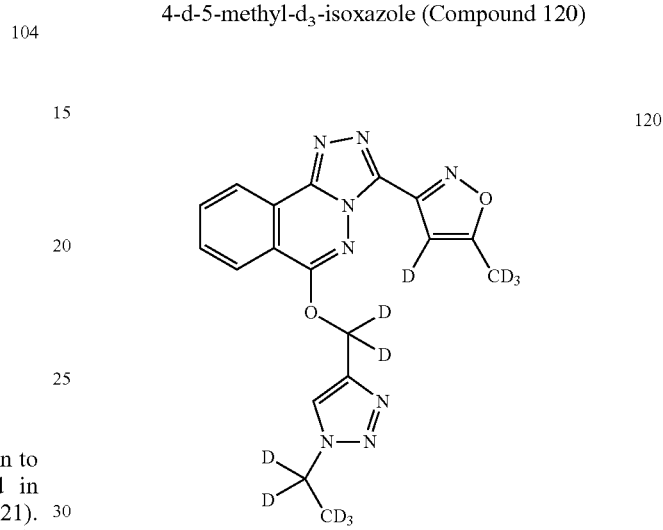

120

Compound 120 was prepared in an analogous fashion to 115 using 15b (prepared as described in Example 18). $^1$H-NMR (300 MHz, CDCl$_3$): δ 7.80 (t, J=6.2, 1H), 7.94 (t, J=6.1, 1H), 8.24 (d, J=6.2, 1H), 8.65 (d, J=6.0, 1H), 8.86 (s, 1H). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.93 min; >95% purity. MS (M+H): 388.2.

Example 9

Synthesis of 3-(6-((1-Ethyl-d$_5$-1H-1,2,3-triazol-4-yl)methoxy-d$_2$)-[1,2,4]triazolo[3,4-a]phthalazin-3-yl)-5-methyl-d$_3$-isoxazole (Compound 110)

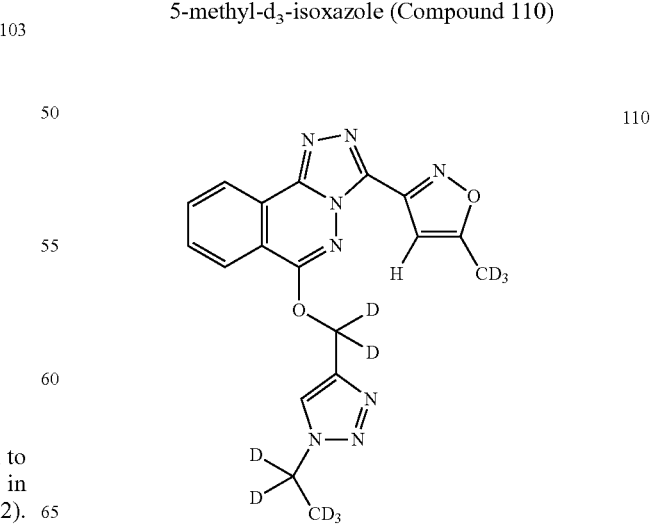

110

Compound 110 was prepared in an analogous fashion to 115 using intermediate 12b (prepared as described in Example 14) and intermediate 15b (prepared as described in Example 15). $^1$H-NMR (300 MHz, CDCl$_3$): δ 6.90 (s, 1H), 7.80 (t, J=7.8, 1H), 7.94 (t, J=7.8, 1H), 8.26 (d, J=8.2, 1H), 8.65 (d, J=8.1, 1H), 8.86 (s, 1H). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.96 min; >94% purity. MS (M+H): 387.3.

Example 10

Synthesis of 3-(6-((1-Ethyl-d$_5$-1H-1,2,3-triazol-4-yl)methoxy)-[1,2,4]triazolo[3,4-a]phthalazin-3-yl)-4-d-5-methyl-d$_3$-isoxazole (Compound 119)

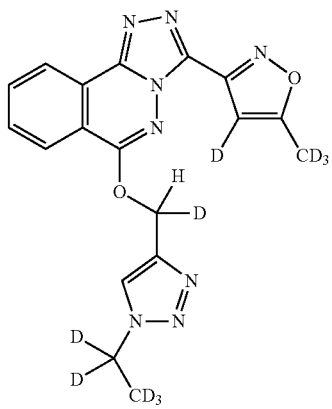

Compound 119 was prepared in an analogous fashion to 115 using 15c (prepared as described in Example 19). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.93 min; >88% purity. MS (M+H): 386.1.

Example 11

Synthesis of 3-(6-((1-Ethyl-d$_5$-1H-1,2,3-triazol-4-yl)methoxy)-[1,2,4]triazolo[3,4-a]phthalazin-3-yl)-5-methylisoxazole (Compound 106)

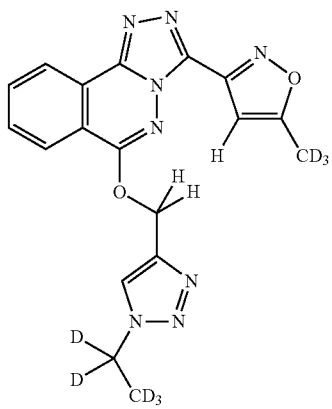

Compound 106 was prepared in an analogous fashion to 115 using 14b (prepared as described in Example 16) and 15c (prepared as described in Example 19). HPLC (method: RP 20 mm C18—gradient method 2—95% ACN+0.1% formic acid in 3.3 min with 1.7 min hold at 95% ACN+0.1% formic acid; wavelength: 254 nm): retention time: 3.11 min; >63% purity. MS (M+H): 382.2.

Example 12

Synthesis of 3-(6-((1-Ethyl-d$_5$-1H-1,2,3-triazol-4-yl)methoxy)-[1,2,4]triazolo[3,4-a]phthalazin-3-yl)-5-methyl-d$_3$-isoxazole (Compound 109)

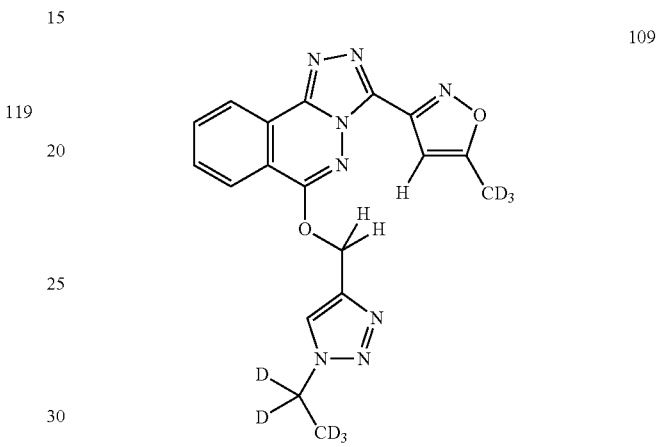

Compound 109 was prepared in an analogous fashion to 115 using intermediate 12b (prepared as described in Example 14) and 15c (prepared as described in Example 19). HPLC (method: RP 20 mm C18—gradient method 2—95% ACN+0.1% formic acid in 3.3 min with 1.7 min hold at 95% ACN+0.1% formic acid; wavelength: 254 nm): retention time: 2.94 min; >89% purity. MS (M+H): 385.2.

Example 13

Synthesis of 4-d-5-Methyl-d$_3$ isoxazole-3-carboxylate (12a)

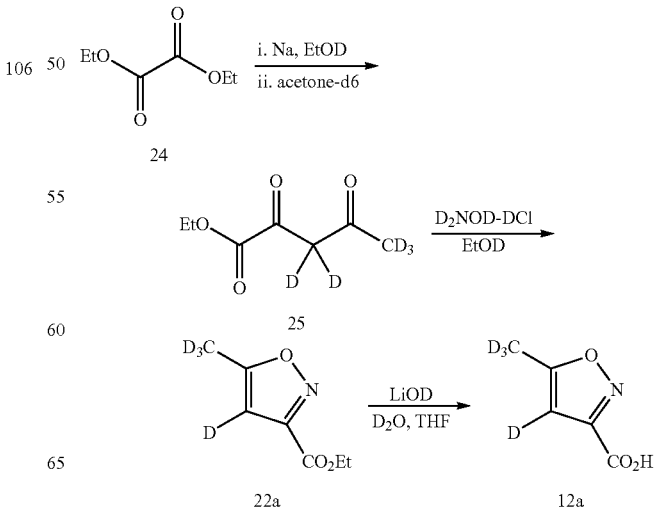

Step 1. Ethyl 3,3,5,5,5-d$_5$-2,4-dioxopentanoate (25)

Sodium metal (0.8 g, 34.8 mmol) was added portion-wise to EtOD (Aldrich, 99 atom % D; 50 mL) at room temperature. The mixture was stirred until all sodium had dissolved. A mixture of 24 (4 mL, 26.8 mmol) and acetone-d$_6$ (Aldrich, 99.9 atom % D; 2.2 mL, 26.8 mmol) was added dropwise to the NaOEt/EtOD solution. The reaction was stirred for 1 hr, quenched with DCl (Cambridge Isotopes, 99 atom % D; 5 mL, 36% in D$_2$O) and concentrated. The residue was diluted in D$_2$O (50 mL) and extracted with EtOAc (3×30 mL). The combined organic phases were dried (Na$_2$SO$_4$) and concentrated to provide 5 g of crude 25.

Step 2. Ethyl 4-d-5-methyl-d$_3$ isoxazole-3-carboxylate (22a)

To a solution of 25 (3.0 g, 18.4 mmol) in EtOD (Aldrich, 99 atom % D; 60 mL) was added hydroxylamine-d$_3$ DCl (CDN Isotopes, 99.4 atom % D; 4.7 g, 64.4 mmol) and the mixture was heated at reflux overnight. The reaction was cooled and concentrated. The residue was diluted with water (10 mL) and ethyl acetate (50 mL) and the layers were separated. The aqueous layer was extracted with ethyl acetate (2×50 mL). The combined organic solution was washed with brine, dried (Na$_2$SO$_4$), and concentrated. The crude material was purified by chromatography on an Analogix automated system (40 g column, 0-20% ethyl acetate/heptane) to afford 2.2 g (74%) of 22a as a clear oil that slowly solidified on standing.

Step 3. 4-d-5-Methyl-d$_3$ isoxazole-3-carboxylate (12a)

Crude 22a (1 g, 6.3 mmol) was dissolved in THF (30 mL) and treated with LiOD (Cambridge Isotopes, 99.5 atom % D; 3N, 5 mL, 15 mmol). The reaction was heated at reflux for 5-6 hr. The solution was cooled and concentrated to remove volatile materials. Saturated citric acid solution was added to adjust the pH to 3 and the product was extracted with ethyl acetate (2×50 mL). The combined organic phase was washed with brine, dried (Na$_2$SO$_4$), and concentrated to provide 200 mg of 12a. Some product remained in the aqueous phase and was not isolated.

Example 14

Synthesis of 5-Methyl-d$_3$-isoxazole-3-carboxylate (12b)

Scheme 6. Preparation of Intermediate 12b.

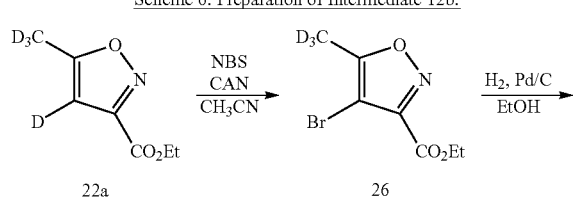

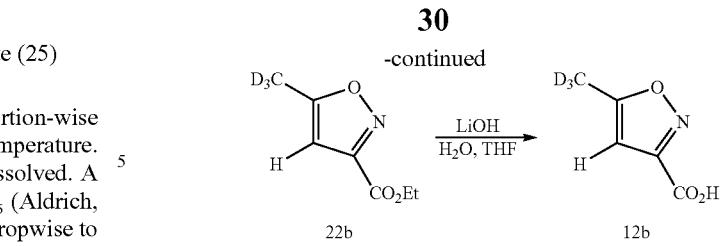

Step 1. Ethyl 4-bromo-5-methyl-d$_3$-isoxazole-3-carboxylate (26)

A mixture of 22a (500 mg, 3.14 mmol), N-bromosuccinimide (NBS, 840 mg, 4.7 mmol) and ammonium cerium (IV) nitrate (CAN, 860 mg, 1.57 mmol) in anhydrous acetonitrile (10 mL) was heated at 80° C. for 24 hr. The reaction showed approximately 55% product by GCMS integration. More NBS (400 mg) was added and the reaction was heated for a further 3-4 hr. Little visible progress by GCMS was observed and the reaction was stopped. The mixture was cooled and concentrated. The residue was partitioned between MTBE (100 mL) and water (20 mL). The aqueous layer was washed with MTBE and the combined organic solution was dried (Na$_2$SO$_4$) and concentrated. Two reactions on the same scale (total 6.28 mmol) were combined and the crude material was purified on an Analogix automated system (40 g column, 0-50% ethyl acetate/heptane) to afford 1.09 g (73%) of 26 as a clear liquid.

Step 2. Ethyl 5-methyl-d$_3$-isoxazole-3-carboxylate (22b)

Compound 26 (1.09 g, 4.6 mmol) was dissolved in ethanol (100 mL), treated with 20% palladium/carbon (50% water, 500 mg) and shaken under a hydrogen atmosphere at 50 psi. After 24 hr the reaction appeared to be complete by GCMS and $^1$H NMR integration. The mixture was filtered through Celite, washing with ethanol, and was concentrated to a residue. The crude material was used directly in the next step without purification.

Step 3. 5-Methyl-d$_3$-isoxazole-3-carboxylate (12b)

Crude 22b (4.6 mmol) was dissolved in THF (15 mL). LiOH (1M, 10 mL) was added and the mixture was heated at 60° C. for 24 hr. The reaction was cooled and the volatile components were removed by evaporation. Saturated aqueous citric acid solution was added to the residue to adjust the pH to 3. The product was extracted with ethyl acetate (2×50 mL), adjusting the pH to 3 if needed between extractions. The combined organic solution was dried and evaporated to give 160 mg of crude 12b. Some product remained in the aqueous phase and was not isolated.

Example 15

Synthesis of N'-(4-Chlorophthalazin-1-yl)-5-methyl-d₃-isoxazole-3-carbohydrazide (13b)

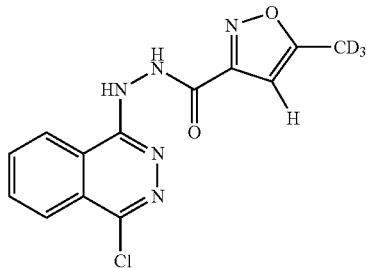

Intermediate 13b was prepared in an analogous fashion to 13a (see Example 1) using 12b (prepared as described in Example 14) in the reaction with 11. MS (M+H): 307.2.

Example 16

6-Chloro-3-(5-methyl-3-isoxazolyl)-1,2,4-triazolo[3,4-a]phthalazine (14b)

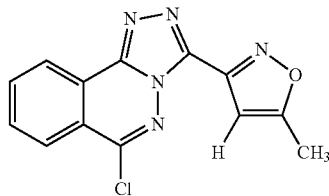

Intermediate 14b was prepared in two steps from intermediate 11 in an analogous fashion to the preparation of intermediate 14a (see Example 1). Commercially available 5-methylisoxazole-3-carboxylic acid (12c) was used in the first step.

Example 17

Synthesis of 3-(6-Chloro-[1,2,4]-triazolo[3,4-a]phthalazin-3-yl)5-methyl-d₃-isoxazole (14c)

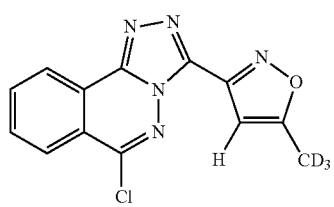

Compound 14c was prepared in an analogous fashion to 14a using crude 13b (prepared as described in Example 15) in the cyclization. MS (M+H): 289.2.

Example 18

Synthesis of (1-Ethyl-d₅-1H-1,2,3-triazol-4-yl)methan-d₂-ol (15b)

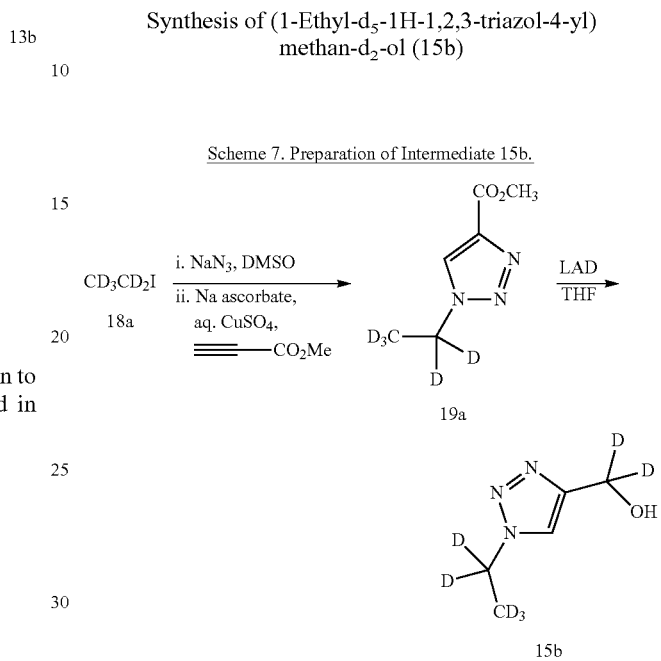

Scheme 7. Preparation of Intermediate 15b.

Step 1. Methyl 1-ethyl-d₅-1H-1,2,3-triazole-4-carboxylate (19a)

A solution of sodium azide in anhydrous dimethyl sulfoxide (0.5 M) was prepared and allowed to stir for 24 hr prior to use. To this solution (4 mL, 2.0 mmol) was added ethyl iodide-d5 (Cambridge Isotopes, 99 atom % D; 160 μL 2.0 mmol) and the reaction was stirred for 6-7 hr. The mixture was diluted with water (5 mL), then sodium ascorbate (40 mg, 0.2 mmol), methyl propiolate (167 μL, 2.0 mmol) and aqueous copper sulfate (1M, 400 μL, 0.4 mmol) were sequentially added. The solution was stirred in a closed flask overnight. Multiple reactions were combined (9 runs×2 mmol) and diluted with ethyl acetate (100 mL total). The layers were separated and the aqueous layer was washed with ethyl acetate. The combined organic solution was dried (Na₂SO₄) and concentrated to provide 2.1 g of crude material which contained residual DMSO as the major impurity. The crude material was purified by chromatography on an Analogix automated system (24 g column, 10-80% ethyl acetate/heptane) to provide 1.19 g (41%) of 19a as a white solid.

Step 2. (1-Ethyl-d₅-1H-1,2,3-triazol-4-yl)methan-d₂-ol (15b)

A solution of 19a (400 mg, 2.5 mmol) in anhydrous THF (10 mL) was cooled to 0° C. in an ice bath. Lithium aluminum deuteride (Isotec, 98 atom % D; 105 mg, 2.5 mmol) was added portion-wise and the reaction was allowed to warm to room temperature. The reaction was checked for completion, then cooled to 0° C. and quenched by the addition of saturated aqueous sodium sulfate solution (2.4 mL). The mixture was stirred at room temperature for 1 hr then filtered through a Celite pad, washing with THF. The filtrate was concentrated and the residue was azeotroped several times from anhydrous ethanol to remove residual water. The crude 15b was used in the next step without further purification.

Example 19

Synthesis of (1-ethyl-$d_5$-1H-1,2,3-triazol-4-yl)methanol (15c)

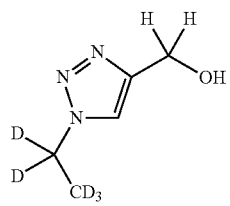

15c

Compound 15c was prepared in an analogous manner to 15b by reduction of 19a with LAH.

Example 20

Synthesis of (1-Methyl-$d_3$-1H-1,2,3-triazol-4-yl)methan-$d_2$-ol (15a)

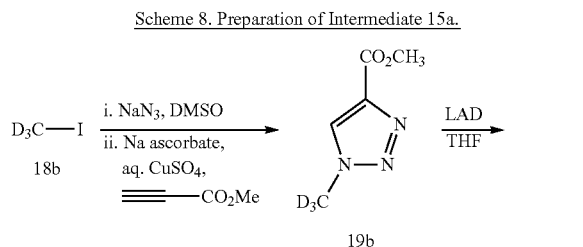

Scheme 8. Preparation of Intermediate 15a.

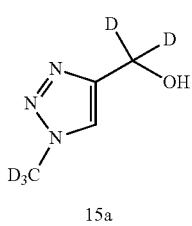

15a

Step 1. Methyl 1-methyl-$d_3$-1H-1,2,3-triazole-4-carboxylate (19b)

Compound 19b was prepared according to the above scheme in an analogous manner to 19a by the addition of iodomethane-$d_3$ (Cambridge Isotopes, 99.5 atom % D; 124 µL, 2.0 mmol) to the sodium azide solution.

Step 2. (1-Methyl-$d_3$-1H-1,2,3-triazol-4-yl)methan-$d_2$-ol (15a)

Compound 15a was prepared according to the above scheme in an analogous manner to 15b by reduction of 19b with LAD (Isotec, 98 atom % D).

Example 21

Synthesis of (1-Methyl-$d_3$-1H-1,2,3-triazol-4-yl)methanol (15d)

Compound 15d was prepared in an analogous fashion to 15a by reduction of 19b with LAH.

Example 22

Synthesis of (1-Methyl-1H-1,2,3-triazol-4-yl)methanol (15e)

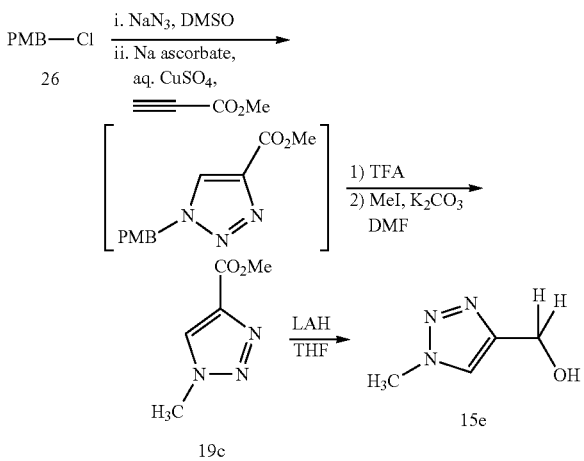

Scheme 9. Preparation of Intermediate 15e.

Step 1. Methyl 1-methyl-1H-1,2,3-triazole-4-carboxylate (19c)

A solution of sodium azide in anhydrous dimethyl sulfoxide (0.5 M) was prepared and allowed to stir for 24 hr prior to use. To this solution (19 mL, 9.5 mmol) was added p-methoxybenzyl chloride (1.29 mL, 9.5 mmol) and the reaction was stirred overnight. The mixture was diluted with water (20 mL), then sodium ascorbate (188 mg, 0.95 mmol), methyl propiolate (795 µL, 9.5 mmol) and aqueous copper sulfate (1M, 1.9 mL, 1.9 mmol) were sequentially added. The solution was stirred in a closed flask overnight. Additional water was added, the mixture was filtered, and the solids were washed with water. Drying gave 2.17 g (92%) of a light greenish/yellow solid. The crude ethyl 1-(4-methoxybenzyl)-1H-1,2,3-triazole-4-carboxylate was then dissolved in TFA (6 mL) and stirred at 60° C. overnight. The solution turned a dark reddish color. The reaction was concentrated and the residual TFA was removed by azeotroping from $CH_2Cl_2$ several times. The residue was diluted with MTBE, filtered and concentrated to provide 1.9 g of 1-methyl-1H-1,2,3-triazole- 4-carboxylate as the TFA salt. The crude salt was dissolved in anhydrous DMF (5 mL) and the solution was cooled to 0° C. Potassium carbonate powder (2.3 g, 17 mmol) and methyl iodide (630 µL, 10.2 mmol) were added and the mixture was allowed to warm to room temperature. After 2 hr the reaction was quenched by the addition of water (5 mL) followed by $CH_2Cl_2$ (25 mL). The layers were separated and the aqueous layer was washed with $CH_2Cl_2$. The combined organic solution was washed with brine, dried ($Na_2SO_4$), and concentrated. The crude material was purified by chromatography on an Analogix automated system (40 g column, 0-80% ethyl acetate/heptane) to provide 300 mg of 19c plus another 190 mg of a mixture of isomers.

Step 2. (1-methyl-1H-1,2,3-triazol-4-yl)methanol (15e)

Compound 15e was prepared according to the above scheme in an analogous fashion to 15b by the reduction of 19c with LAH.

Example 23

Alternate Synthesis of Intermediate Methyl 1-Methyl-1H-1,2,3-triazole-4-carboxylate (19c)

19c was alternatively prepared in one step in a manner analogous to 19b (Example 17, Step 1) using iodomethane Example 24

Evaluation of Metabolic Stability in Human Liver Microsomes

Human liver microsomes (20 mg/mL) are available from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are available from Sigma-Aldrich.

7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for α5IA and the positive control, 7-ethoxycoumarin (1 µM). Testing is done in triplicate.

The in vitro $t_{1/2}$s for test compounds are calculated from the slopes of the linear regression of % parent remaining (ln) vs incubation time relationship:

in vitro $t_{1/2} = 0.693/k$ $k = -$[slope of linear regression of % parent remaining (ln)vs incubation time].

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of Formula Ia,

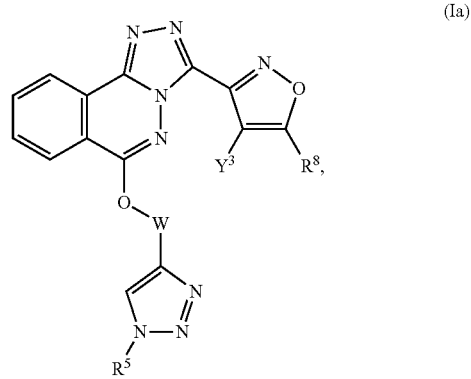

(Ia)

or a pharmaceutically acceptable salt thereof, wherein:
$R^5$ is selected from $CD_3$ and $CH_3$;
$R^8$ is $CD_3$;
W is —$CY^1Y^2$—, wherein $Y^1$ and $Y^2$ are the same and are selected from hydrogen and deuterium; and
$Y^3$ is hydrogen or deuterium;
wherein there is at least 50.1% incorporation of deuterium at any atom designated as D or deuterium.

2. The compound of claim 1, wherein $Y^3$ is hydrogen and W, $R^5$, and $R^8$ are as defined in the table below:

| Compound | W | $R^5$ | $R^8$ |
|---|---|---|---|
| 102 | $CD_2$ | $CH_3$ | $CD_3$ |
| 103 | $CH_2$ | $CH_3$ | $CD_3$ |
| 104 | $CH_2$ | $CD_3$ | $CD_3$ |
| 105 | $CD_2$ | $CD_3$ | $CD_3$ | or a pharmaceutically acceptable salt thereof.

3. The compound of claim 1, wherein $Y^3$ is deuterium and W, $R^5$, and $R^8$ are as defined in the table below:

| Compound | W | $R^5$ | $R^8$ |
|---|---|---|---|
| 112 | $CD_2$ | $CH_3$ | $CD_3$ |
| 113 | $CH_2$ | $CH_3$ | $CD_3$ |
| 114 | $CH_2$ | $CD_3$ | $CD_3$ |
| 115 | $CD_2$ | $CD_3$ | $CD_3$ | or a pharmaceutically acceptable salt thereof.

4. The compound of claim 1, wherein any atom not designated as deuterium in any of the embodiments set forth above is present at its natural isotopic abundance.

5. A pyrogen-free pharmaceutical composition comprising a compound of claim 1 or a pharmaceutically acceptable salt of said compound; and a pharmaceutically acceptable carrier.

* * * * *